(12) United States Patent
Hultgren et al.

(10) Patent No.: US 7,716,024 B2
(45) Date of Patent: May 11, 2010

(54) METHOD AND APPARATUS FOR ELECTRONICALLY GENERATING A COLOR DENTAL OCCLUSION MAP WITHIN ELECTRONIC MODEL IMAGES

(75) Inventors: Bruce Willard Hultgren, Victoria, MN (US); Timothy W. Vadnais, Victoria, MN (US); Michael Craig Marshall, Savage, MN (US); Robert J. Isaacson, Edina, MN (US)

(73) Assignee: GeoDigm Corporation, Chanhassen, MN (US)

( * ) Notice: Subject to any disclaimer, the term of this patent is extended or adjusted under 35 U.S.C. 154(b) by 538 days.

(21) Appl. No.: 10/426,252

(22) Filed: Apr. 29, 2003

(65) Prior Publication Data

US 2003/0214501 A1 Nov. 20, 2003

(51) Int. Cl.
G06G 7/48 (2006.01)
(52) U.S. Cl. .......................................... 703/6
(58) Field of Classification Search ...................... 703/6
See application file for complete search history.

(56) References Cited

U.S. PATENT DOCUMENTS

| 3,084,438 | A | 4/1963 | Goodfriend |
| 4,123,768 | A | 10/1978 | Kilshaw et al. ............. 354/292 |
| 4,123,786 | A | 10/1978 | Cramer |
| 4,182,312 | A | 1/1980 | Mushabac .................... 433/68 |
| 4,402,326 | A | 9/1983 | Okano et al. |
| 4,436,684 | A | 3/1984 | White |
| 4,575,805 | A | 3/1986 | Moermann et al. |
| 4,611,288 | A | 9/1986 | Duret et al. ................ 364/474 |
| 4,673,352 | A | 6/1987 | Hansen |
| 4,742,464 | A | 5/1988 | Duret et al. |
| 4,752,964 | A | 6/1988 | Okada et al. ................... 382/1 |
| 4,775,946 | A | 10/1988 | Anjyo ........................ 364/522 |
| 4,799,785 | A | 1/1989 | Keates et al. ................ 351/212 |
| 4,837,732 | A | 6/1989 | Brandestini et al. |
| 4,862,371 | A | 8/1989 | Maekawa .............. 364/431.11 |

(Continued)

FOREIGN PATENT DOCUMENTS

IS 120867 5/1997

(Continued)

OTHER PUBLICATIONS

Rodger et al. "Choosing Rendering Parameters for Effective Communication of 3d Shape". IEEE 2000.*

(Continued)

*Primary Examiner*—Kamini S Shah
*Assistant Examiner*—Saif A Alhija
(74) *Attorney, Agent, or Firm*—Merchant & Gould P.C.

(57) ABSTRACT

A method, apparatus, and article of manufacture provide a system for electronically generating a color dental occlusion map within electronic model images. With the advances recently made computational systems, these computer based image systems may be used to permit end users to replace paper and physical models with electronic images. A mechanism to capture image representations of physical objects accurately and with sufficient resolution is provided in a form that is both inexpensive to operate while providing rapid turn-around for users. Second, a mechanism to visually display interaction between parts of an object is also provided. These features are expressly addressed for impressions of human teeth that are scanned to allow electronic images of the models of a patient's teeth to be represented and manipulated.

24 Claims, 12 Drawing Sheets

U.S. PATENT DOCUMENTS

| | | | |
|---|---|---|---|
| 4,862,391 A | 8/1989 | Ohhashi | 364/522 |
| 4,935,635 A | 6/1990 | O'Harra | 250/560 |
| 4,983,120 A | 1/1991 | Coleman et al. | 433/24 |
| 5,020,993 A | 6/1991 | Levandoski | 433/65 |
| 5,027,281 A | 6/1991 | Rekow et al. | |
| 5,113,424 A | 5/1992 | Burdea et al. | |
| 5,121,333 A | 6/1992 | Riley et al. | |
| 5,150,457 A | 9/1992 | Behm et al. | 395/120 |
| 5,184,306 A | 2/1993 | Erdman et al. | 364/474.05 |
| 5,198,827 A | 3/1993 | Seaton | |
| 5,198,877 A | 3/1993 | Schulz | 356/375 |
| 5,224,049 A | 6/1993 | Mushabac | 364/474.05 |
| 5,257,203 A | 10/1993 | Riley et al. | 364/474.05 |
| 5,267,293 A | 11/1993 | Virta | |
| 5,273,429 A | 12/1993 | Rekow et al. | |
| 5,338,198 A | 8/1994 | Wu et al. | 433/213 |
| 5,340,309 A | 8/1994 | Robertson | 433/69 |
| 5,343,391 A | 8/1994 | Mushabac | 364/413.28 |
| 5,347,454 A | 9/1994 | Mushabac | 364/413.28 |
| 5,359,511 A | 10/1994 | Schroeder et al. | |
| 5,368,478 A | 11/1994 | Andreiko et al. | |
| 5,372,502 A | 12/1994 | Massen et al. | |
| 5,395,238 A | 3/1995 | Andreiko et al. | |
| 5,416,822 A | 5/1995 | Kunik | |
| 5,431,562 A | 7/1995 | Andreiko et al. | 433/24 |
| 5,440,393 A | 8/1995 | Wenz | 356/376 |
| 5,442,572 A | 8/1995 | Kiridena et al. | 364/560 |
| 5,447,432 A | 9/1995 | Andreiko et al. | 433/24 |
| 5,448,472 A | 9/1995 | Mushabac | 364/413.28 |
| 5,454,068 A | 9/1995 | Ramanujam | 395/119 |
| 5,454,717 A | 10/1995 | Andreiko et al. | 433/24 |
| 5,458,487 A | 10/1995 | Komatsu et al. | 433/71 |
| RE35,169 E | 3/1996 | Lemchen et al. | |
| 5,518,397 A | 5/1996 | Andreiko et al. | |
| 5,533,895 A | 7/1996 | Andreiko et al. | |
| 5,549,476 A | 8/1996 | Stern | |
| 5,562,448 A | 10/1996 | Mushabac | 433/215 |
| 5,569,578 A | 10/1996 | Mushabac | |
| 5,588,430 A | 12/1996 | Bova et al. | |
| 5,605,459 A | 2/1997 | Kuroda et al. | 433/214 |
| 5,683,243 A | 11/1997 | Andreiko et al. | 433/3 |
| 5,730,151 A | 3/1998 | Summer et al. | |
| 5,800,174 A | 9/1998 | Andersson | |
| 5,823,778 A | 10/1998 | Schmitt et al. | |
| 5,842,858 A | 12/1998 | Truppe | |
| 5,879,158 A | 3/1999 | Doyle et al. | |
| 5,880,962 A | 3/1999 | Andersson et al. | |
| 5,882,192 A | 3/1999 | Bergersen | |
| 5,905,658 A | 5/1999 | Baba | 364/578 |
| 5,977,979 A | 11/1999 | Clough et al. | 345/422 |
| 5,989,199 A | 11/1999 | Cundari et al. | 600/587 |
| 6,015,289 A | 1/2000 | Andreiko et al. | 433/3 |
| 6,068,482 A | 5/2000 | Snow | |
| 6,123,544 A | 9/2000 | Cleary | |
| 6,143,003 A | 11/2000 | Cosman | |
| 6,152,731 A | 11/2000 | Jordan et al. | |
| 6,217,334 B1 | 4/2001 | Hultgren | |
| 6,227,850 B1 | 5/2001 | Chishti et al. | |
| 6,244,861 B1 | 6/2001 | Andreiko et al. | 433/3 |
| 6,250,918 B1 | 6/2001 | Sachdeva et al. | |
| 6,318,994 B1 | 11/2001 | Chisti et al. | |
| 6,322,359 B1 | 11/2001 | Jordan et al. | 433/73 |
| 6,322,728 B1 | 11/2001 | Brodkin et al. | 264/19 |
| 6,334,853 B1* | 1/2002 | Kopelman et al. | 600/590 |
| 6,364,660 B1 | 4/2002 | Durbin et al. | |
| 6,371,761 B1 | 4/2002 | Cheang et al. | |
| 6,406,292 B1 | 6/2002 | Chishti et al. | 433/24 |
| 6,409,504 B1* | 6/2002 | Jones et al. | 433/24 |
| 6,436,684 B1 | 8/2002 | Woodage et al. | |
| 6,450,807 B1 | 9/2002 | Chishti et al. | |
| 6,471,511 B1 | 10/2002 | Chishti et al. | |
| 6,554,613 B1 | 4/2003 | Sachdeva et al. | |
| 6,579,095 B2 | 6/2003 | Marshall et al. | |
| 6,602,070 B2 | 8/2003 | Miller et al. | |
| 6,608,628 B1 | 8/2003 | Ross et al. | |
| 6,632,089 B2 | 10/2003 | Rubbert et al. | |
| 6,648,640 B2 | 11/2003 | Rubbert et al. | |
| 6,688,886 B2 | 2/2004 | Hughes et al. | |
| 6,726,478 B1 | 4/2004 | Isiderio et al. | |
| 6,783,360 B2 | 8/2004 | Chishti | |
| 6,905,337 B1 | 6/2005 | Sachdeva | |
| 6,925,198 B2 | 8/2005 | Scharlack et al. | |
| 7,362,890 B2 | 4/2008 | Scharlack et al. | |
| 2001/0002310 A1 | 5/2001 | Chishti et al. | |
| 2002/0015934 A1 | 2/2002 | Rubbert et al. | |
| 2002/0031743 A1 | 3/2002 | Kim | |
| 2002/0081554 A1 | 6/2002 | Marshall et al. | |
| 2003/0224316 A1 | 12/2003 | Marshall | |
| 2004/0015327 A1 | 1/2004 | Sachdeva et al. | |
| 2004/0023183 A1 | 2/2004 | Miller et al. | |
| 2004/0066877 A1 | 4/2004 | Arai et al. | |
| 2004/0110110 A1 | 6/2004 | Chishti et al. | |
| 2005/0019721 A1 | 1/2005 | Chishti | |
| 2005/0028826 A1 | 2/2005 | Palmisano | |
| 2005/0095562 A1 | 5/2005 | Sporbert et al. | |
| 2005/0153255 A1 | 7/2005 | Sporbert et al. | |
| 2005/0271996 A1 | 12/2005 | Sporbert et al. | |
| 2008/0002869 A1 | 1/2008 | Scharlack et al. | |

FOREIGN PATENT DOCUMENTS

| | | |
|---|---|---|
| IS | 120892 | 5/1997 |
| IS | 121872 | 9/1997 |
| WO | WO 98/32394 | 7/1998 |

OTHER PUBLICATIONS

Travers et al. "Associations Between Incisor and Mandibular Condylar Movements During Maximum Mouth Opening in Humans" 2000 Elsevier Science Ltd.*

Kunii, T. et al., "Articulation simulation for an Intelligent Dental Care System", *Displays*, vol. 15, No. 3, pp. 181-188, (1994).

Baker, H. Harlyn, "Building, Visualizing, and Computing on Surfaces of Evolution". *Institute of Electrical and Electronics Engineers, Inc. Computer Graphics and Applications, Modeling and Display of Empiral Data Plus Data Structures, Part II*, cover page and pp. 31-41 (Jul. 1988).

Hayashi, T. et al., "A Computerized System for Analyzing Occlusal Relations During Mandibular Movements", *The International Journal of Prosthodontics*, vol. 7, No. 2, cover page and pp. 108-114 (Mar./Apr. 1994).

Sakaguchi, R. et al., "Digital Imaging of Occlusal Contacts in the Intercuspal Position", *Journal of Prosthodontics*, vol. 3, No. 4, cover page and pp. 193-197 (Dec. 1994).

Leinfelder, K. et al., "A new method for generating ceramic restorations: a CAD-CAM System", *Journal of the American Dental Association*, vol. 118, cover page and pp. 703-707, (Jun. 1989).

Andrews, L., "The six keys to normal occlusion", *American Journal of Orthodontics*, vol. 62, No. 3, cover page, table of contents, and pp. 296-309 (Sep. 1972).

Larkin, J.D., "Means for measuring the interocclusal distance", *The Journal of Prosthetic Dentistry*, vol. 17, No. 3, pp. 247-250 (Mar. 1967).

Rekow, D., "Computer-aided design and manufacturing in dentistry; a review of the state of the art", *The Journal of Prosthetic Dentistry*, vol. 58, No. 4, cover page and pp. 513-516 (Oct. 1987).

Hibi, H. et al., "An optical system for measuring inclination and area of occlusal facets", *Journal of Oral Rehabilitation*, vol. 24, No. 9, cover page and pp. 673-677 (Sep. 1997).

Kuroda et al., "Three-dimensional dental cast analyzing system using laser scanning", *American Journal of Orthodontics and Dentofacial Orthopedics*, vol. 110, No. 4, cover page, table of contents, and pp. 365-369 (Oct. 1996).

Siirilä, H.S. et al., "A photographic method for measuring interocclusal clearance", *Suom. Hammaslää, Toim.* vol. 66, No. 3, pp. 177-182 (1970), English Summary, p. 181.

Tekscan, T-Scan II "Dental Division Overview", Online Tekscan System brochure, Retrieved from http://tekscan.com/dental.html, pp. 1-2, (Oct. 3, 2002).

Tekscan, The T-Scan II "The Future Force in Occlusal Diagnostics", Online Tekscan System brochure, Retrieved from http://www.tekscan.com/dental/system.html, pp. 1-9 (Oct. 3, 2002).

OrthoCad, "Virtual Set-Up", OrthoCad advertisement, 1 page (admitted by Applicants as prior art as of the filing date).

M. Naeije et al., OKAS-3D: Optoelectronic Jaw Movement Recording System with Six Degrees of Freedom; Medical & Biological Engineering & Computing, Sep. 1995, 33, 683-688.

Deng, Y. et al., "Occlusal Contact Changes Before and After Orthodontic Treatment of a Group of Child & Adolescent Patients with TMJ Disturbance," *Australian Orthodontic Journal*, vol. 13, No. 4, pp. 231-237 (Mar. 1995).

Rekow, D., "Comptuer-aided design and manufacturing in dentistry: A review of the state of the art," *The Journal of Prosthetic Dentistry*, vol. 58, No. 4, pp. 512-516 (Oct. 1987).

Seymour, K. et al., "Assessment of shoulder dimensions and angles of porcelain bonded to metal crown preparations," *The Journal of Prosthetic Denistry*, vol. 75, No. 4, pp. 406-411 9 (Apr. 1996).

Sohmura, T. et al., "Use of CAD/CAM System to Fabricate Dental Prostheses. Part 1: CAD for a Clinical Crown Restoration," *The International Journal of Prosthodontics*, vol. 8, No. 3, pp. 252-258 (1995).

Wenzel, A. et al., "Accuracy of caries diagnosis in digital images from charge-coupled device and storage phosphor systems: an in vitro study," *Dentomaxillofac. Radiol.*, vol. 24, No. 4, pp. 250-254 (1995).

Alcaniz, M. et al., "An Advanced System for the Simulation and Planning of Orthodontic Treatment," *Medical Image Analysis*, vol. 2, No. 1, pp. 61-77 (Mar. 1998) (1 page abstract).

Alcaniz, M. et al., "A System for the Simulation and Planning of Orthodontic Treatment Using a Low Cost 3D Laser Scanner for Dental Anatomy Capturing," *Studies in Health Technology and Informatics*, vol. 62, pp. 8-14 (1999) (1 page abstract).

Jones, M. et al., "A Validated Finite Element Method Study of Orthodontic Tooth Movement in the Human Subject," *Journal of Orthodontics*, vol. 28. No. 1, pp. 29-38 (Mar. 2001) (1 page abstract).

Kimura, H. et al., "Three-Dimensional Shape Measurement of Teeth. On the Measurement by the Laser Displacement Meter which is able to Move on Z-direction," *Journal of the Japanese Society for Dental Materials and Devices*, vol. 8, No. 6, pp. 877-882 (Nov. 1989) (1 page abstract).

Kimura, H. et al., "Three-Dimensional Shape Measurement of Teeth. Measurement of Tooth Model by Tilting Method by Means of the Double Sensor Laser Displacement Meter, and the Simulation of Occlusion," *Journal of the Japanese Society for Dental Materials and Devices*, vol. 9, No. 4, pp. 679-686 (Jul. 1990) (1 page abstract).

Kuroda, T. et al.,"Three-dimensional dental cast analyzing system using laser scanning," *American Journal of Orthodontics and Dentofacial Orthopedics*, vol. 110, No. 4, cover page, table of contents, and pp. 365-369 (Oct. 1996).

Laurendeau, D. et al., "A Computer-Vision Technique for the Acquisition and Processing of 3-D Profiles of Dental Imprints: An Application in Orthodontics,"*IEEE Transactions on Medical Imaging*, vol. 10, No. 3, pp. 453-461 (Sep. 1991).

Palmer, R. "CAD/CAM Dental Technology's Future?," *Dental Lab Products*, pp. 14-18 (May/Jun. 2002).

Santler, G. et al., "Indications and Limitations of Three-Dimensional Models in Cranio-Maxillofacial Surgery," *Journal of Cranial-Maxillo-Facial Surgery*, vol. 26, No. 1, pp. 11-16 (Feb. 1998) (1 page abstract).

Schirmer, U. et al., "Manual and Computer-Aided Space Analysis: A Comparative Study," *American Journal of Orthodontics and Dentofacial Orthopedics*, vol. 112, No. 6, pp. 676-680 (Dec. 1997) (1 page abstract).

\* cited by examiner

METHOD AND APPARATUS FOR ELECTRONICALLY GENERATING A COLOR DENTAL OCCLUSION MAP WITHIN ELECTRONIC MODEL IMAGES

TECHNICAL FIELD

The invention relates generally to a distributed computing system for the creation and distribution of electronic models of objects and more particularly to a system, method and article of manufacture for electronically generating a color dental occlusion map within electronic model images.

BACKGROUND

Computational resources available for use by various end users of computing systems has increased significantly. This increase in capability of systems has created the ability for many more end users to utilize computer based image systems to replace processes that utilize paper and physical model processes. In the past, computer aided design, drafting, and manufacture (CAD/CAM) tools represented an area of applications in which computer based image systems have migrated from paper and model based processes to electronic systems.

These CAD/CAM system typically consist of design and drafting tools that allow technical designers to build systems that were previously designed on paper using draftsmen. Over time, the computing system and their respective tools have allowed increasing interactive manipulation of components during the design process. This advance in design of items that are then manufactured has occurred using these computer aided systems.

These CAD/CAM systems, however, typically start their processes with a set of predefined libraries of components that may be used by the user of the computing system. For example, electronic schematics possess a library of components that are used to specify a circuit and its layout. The creation of these libraries, as well as the amount of computational resources needed to perform the operations related to these systems, has prevented the widespread use of these systems in other areas of technology.

With the advances recently made computational systems, these computer based image systems may be used to permit end users to replace paper and physical models with electronic images. Two areas of technology present additional obstacles to the more wide-spread use of these systems. First, a mechanism to capture image representations of physical objects accurately and with sufficient resolution is needed in a form that is both inexpensive to operate while providing rapid turn-around for users. Second, a mechanism to visually display interaction between parts of an object is needed. This problem is especially acute when impressions of human teeth are to be scanned to allow electronic images of the models of a patient's teeth to be represented and manipulated as individual teeth. Neither of these latter obstacles have been overcome in existing imaging systems.

SUMMARY

The present invention relates to a method, apparatus, and article of manufacture for electronically generating a color dental occlusion map within electronic model images.

Other embodiments of a system in accordance with the principles of the invention may include alternative or optional additional aspects. One such aspect of the present invention is a method and computer data product encoding instructions for automatically determining the location of individual teeth within an electronic model image of a patient's mouth to allow the manipulation of the electronic model images by end users. The method determines possible horizontal cut lines within a horizontal plane cut through the electronic model image corresponding to possible separation lines between teeth, determines possible vertical cut lines within a vertical plane cut through the electronic model image corresponding to possible separation lines between teeth, and automatically determines the locations of individual teeth using the possible horizontal cut lines and the possible vertical cut lines.

These and various other advantages and features of novelty which characterize the invention are pointed out with particularity in the claims annexed hereto and form a part hereof. However, for a better understanding of the invention, its advantages, and the objects obtained by its use, reference should be made to the drawings which form a further part hereof, and to accompanying descriptive matter, in which there are illustrated and described specific examples of an apparatus in accordance with the invention.

DETAILED DESCRIPTION

The present invention relates to a code generation method, apparatus, and article of manufacture for providing a distributed computing system for the creation and distribution of electronic models of objects including a system, method and article of manufacture for electronically generating a color dental occlusion map within electronic model images.

Figure 1:
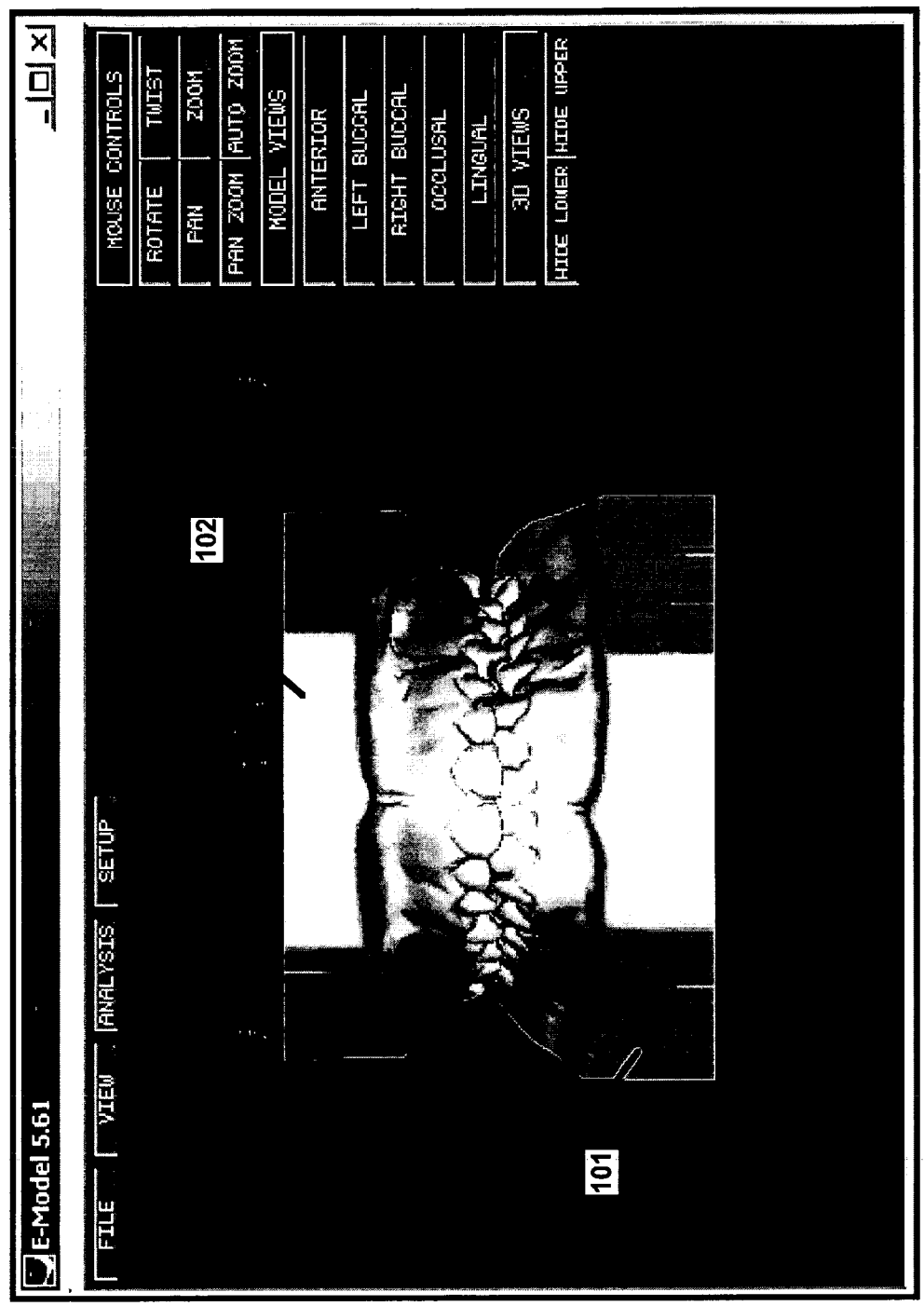
FIG. 1 illustrates an electronic model image of a patient's mouth in which individual teeth have been identified and moved locations in support of a plan of treatment according to one embodiment of the present invention.

FIG. 1 illustrates an electronic model image of a patient's mouth in which individual teeth have been identified and moved locations in support of a plan of treatment according to one embodiment of the present invention. An electronic model of a patient's upper teeth are shown 101 as they are located within a patient's mouth in position relative to a corresponding model of the patient's lower teeth 102. In order for this process to occur, two events must occur. First, an electronic model for the teeth must be generated. This occurs when a physical mold or impression of the mouth is generated. This impression is then electronically scanned to generate the model. The process for generating an electronic model for the teeth is described in commonly assigned U.S. patent application entitled "METHOD AND APPARATUS FOR ELECTRONIC DELIVERY OF DENTAL IMAGES", Ser. No. 09/846,037 filed Apr. 29, 2001, which is incorporated by reference.

Once the electronic model has been generated for the impression, the locations of the individual teeth relative to opposing teeth in the opposite jaw may be determined. Generally, locations where these teeth first make contact as the jaws close is of particular interest. Because these upper and low teeth are known within a common coordinate system, these locations may be easily determined and these points of interest marked for viewing. These points of interest are typically marked with a different color that indicates the distance between the teeth as the jaw is closing.

Figure 2A:
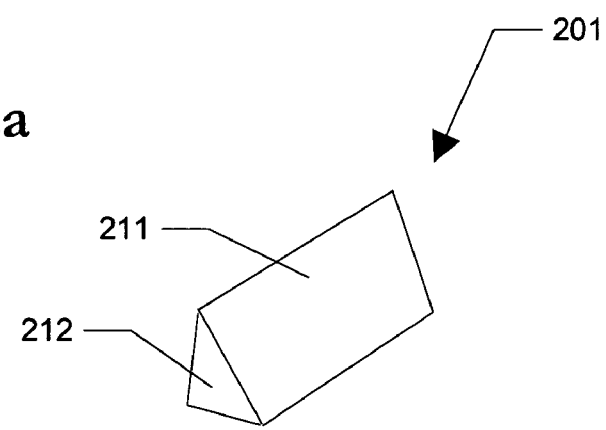
FIGS. 2a-2b illustrates an example of an object from which an electronic model is generated according to yet another example embodiment of the present invention.
Figure 2B:
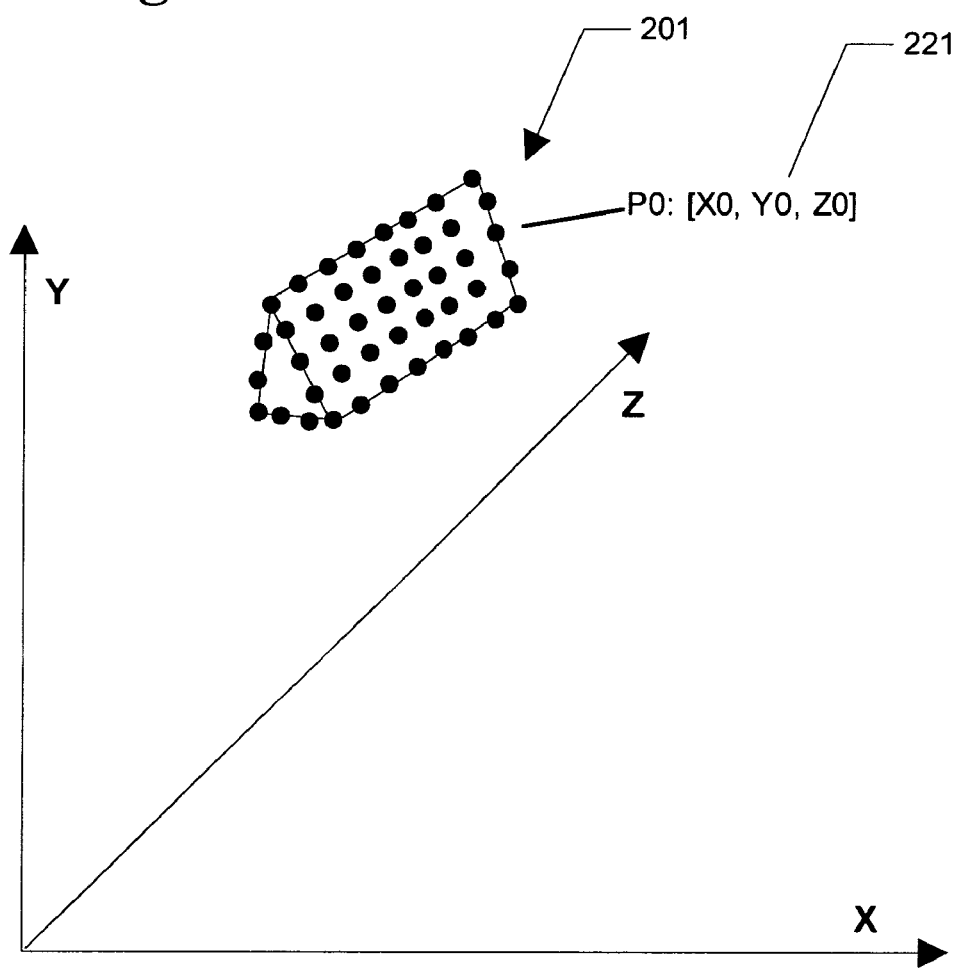

FIGS. 2a-2b illustrates an example of an object from which an electronic model is generated according to yet another example embodiment of the present invention. A simple geometric 3D shape 201 is presented as an example of how a reduced polygonal mesh is generated that may be used as an electronic model. This shape 201 has two visible faces: a small triangular side face 212 and a larger rectangular face 211. Three other faces that are not visible from the perspective shown in FIG. 2a make up this simple object.

FIG. 2b shows this object 201 having a set of surface data points superimposed upon the object 201 faces. When a laser line scanner passes its sensor over a face of the object 201, a line of points corresponding to the position of the objects' surface are obtained. These points are separated by the spatial resolution of the scanner. The data points, P0 221 are specified using a 3 coordinate position X0, Y0, Z0. As the object 201 is moved within the scanning area of the multi-axis platform, the scanner translates the data points to a common coordinate system such that the collection of all points represents the points in a 3D coordinate system that corresponds to the surface of the item 201. These data points are contained within the point cloud data file 500.

Figure 3:
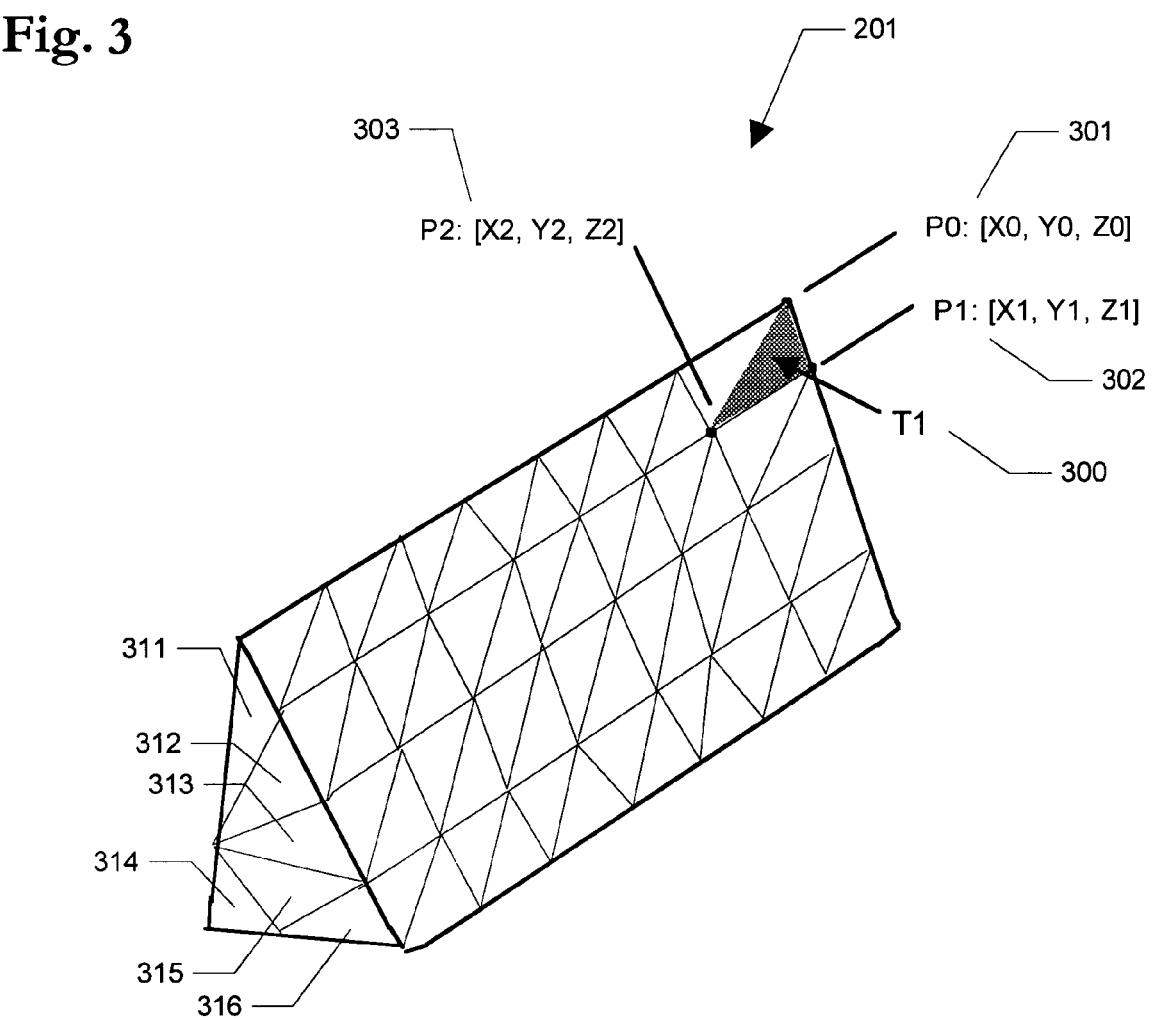
FIG. 3 illustrates a representation of the object in FIG. 2 using a polygonal mesh according to an embodiment of the present invention.

FIG. 3 illustrates a representation of the object in FIG. 2 using a polygonal mesh according to an embodiment of the present invention. As discussed above, the point cloud data file 500 is reduced to a polygonal mesh of triangles in which the surface of the triangles are used to approximate the surface of the item 201. In this example, a triangle, T1 300, is located on the larger surface 211 of the item 201. The triangle T1 300 is specified using the three corner points P0 301, P1 302, and P3 303. As before, each of these three points are specified using a 3D coordinate system such that T1 300 is defined:

T1: {P0, P1, P2} or

T1: {[X0, Y0, Z0], [X1, Y1, Z1], {[X2, Y2, Z2]}.

Each triangle in the polygonal mesh is specified using the three points as shown above. No particular order for the points making up the triangle is necessary. The smaller side 212 of the item 211 in this example is initially shown with six triangles 311-316. The triangles in the polygonal mesh may be created using any number of well known methods for reducing point position data into a polygonal mesh that approximates the surface of the object.

Figure 4:
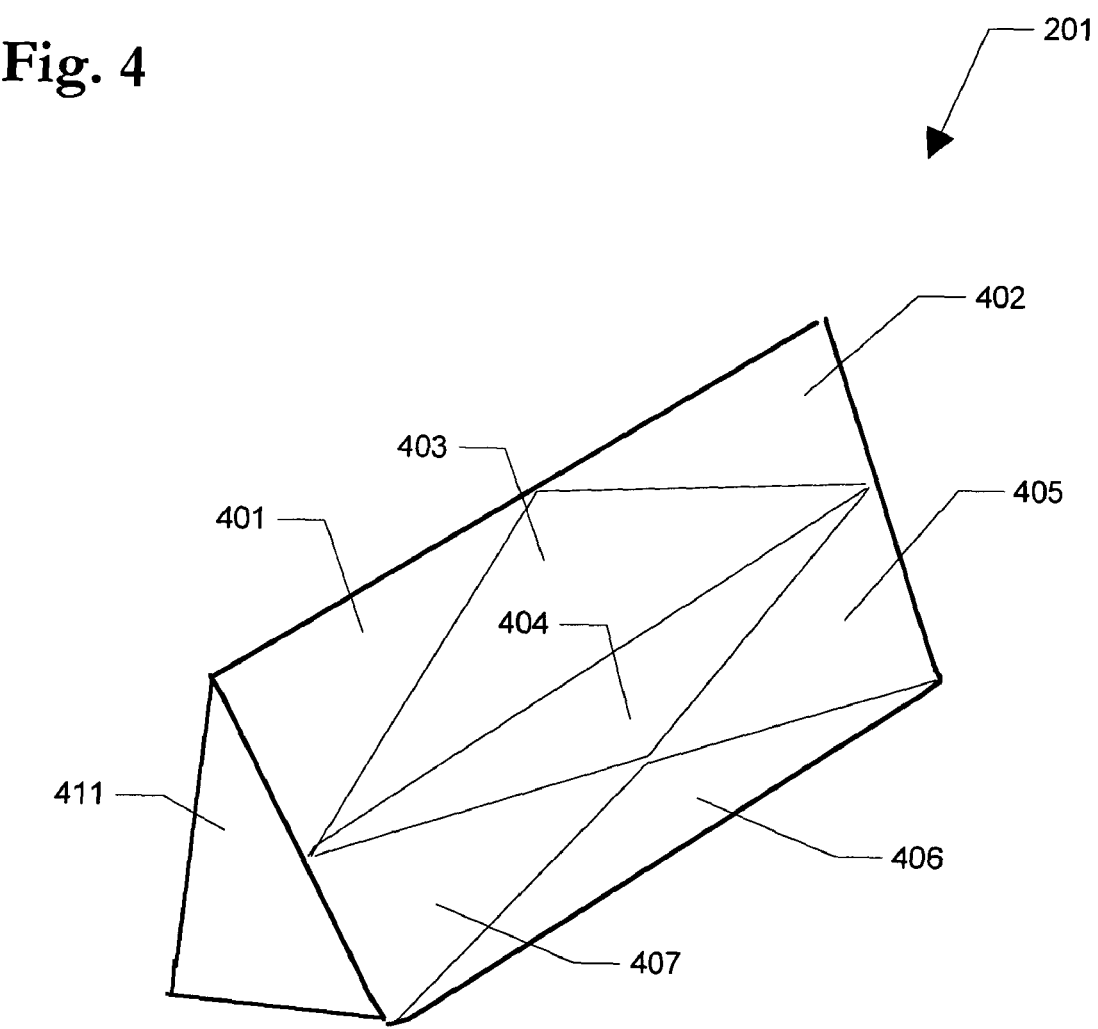
FIG. 4 illustrates a simplified representation of the object in FIG. 2 using a reduced polygonal mesh according to yet another example embodiment of the present invention.

FIG. 4 illustrates a simplified representation of the object in FIG. 2 using a reduced polygonal mesh according to yet another example embodiment of the present invention. A reduced polygonal mesh is generated by combining adjacent triangles in the original polygonal mesh when the two or more triangles are sufficiently coplanar that they may be represented using a single triangle. In this example, a large number of small triangles may have been originally generated mesh shown in FIG. 3. When a flat surface of the simple object 201 is considered, the number of triangles needed is reduced significantly 401-407. In the example, all of the small triangles from the small side 212 of the item 201 have been combined into a single triangle 411. The processing associated with this filtering operation controls the amount of triangle combination by setting a threshold relating to the minimum amount of deviation from a single plane for the two or more triangles that is permitted before two or more triangles are required to remain separate. This filtering process may be accomplished using a number of commercially available polygonal mesh processing products without deviating from the present invention as recited within the attached claims.

Figure 5:
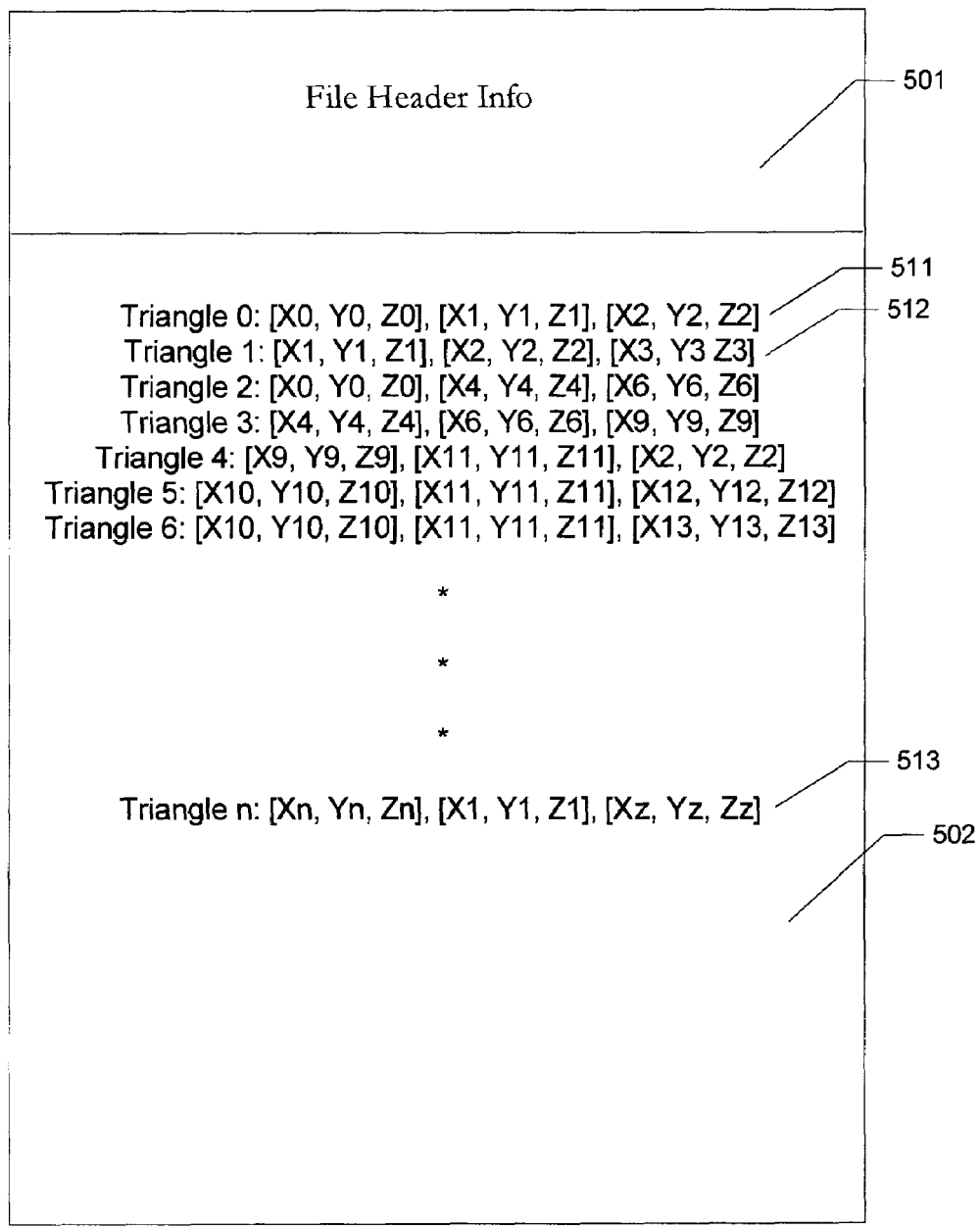
FIG. 5 illustrates a format for an electronic model data file according to yet another example embodiment of the present invention.

FIG. 5 illustrates a format for an electronic model data file according to yet another example embodiment of the present invention. The electronic model data file 500 consists of a file header info block 501 and a triangle specification block 502. The triangle specification block consists of the set of triangle definitions 511-513 that are used to define the reduced polygonal mesh.

The file header info block 501 includes a set of searchable identification information that may be used to identify a particular model from any number of related models. The mouth and teeth electronic models, for example, will likely contain patient identification information such as name, date of birth, address, social security number that may be used to uniquely identify the patient from which the model was generated. The info block 511 may also contain dental care provider information such as the dentist name and address as well as the date on which the impression was taken that generated the electronic model.

The file header info block 501 includes a set of searchable identification information that may be used to identify a particular model from any number of related models. The mouth and teeth eModels, for example, will likely contain patient identification information such as name, date of birth, address, social security number that may be used to uniquely identify the patient from which the model was generated. The info block 511 may also contain dental care provider information such as the dentist name and address as well as the date on which the impression was taken that generated the eModel.

This data file 500 is typically ASCII encoded data that may be easily searched and processed as necessary. One skilled in the art will recognize how this file header info block 501 may be modified to include any information needed by a particular application without deviating from the spirit and scope of the present invention as recited within the attached claims.

Figure 6:
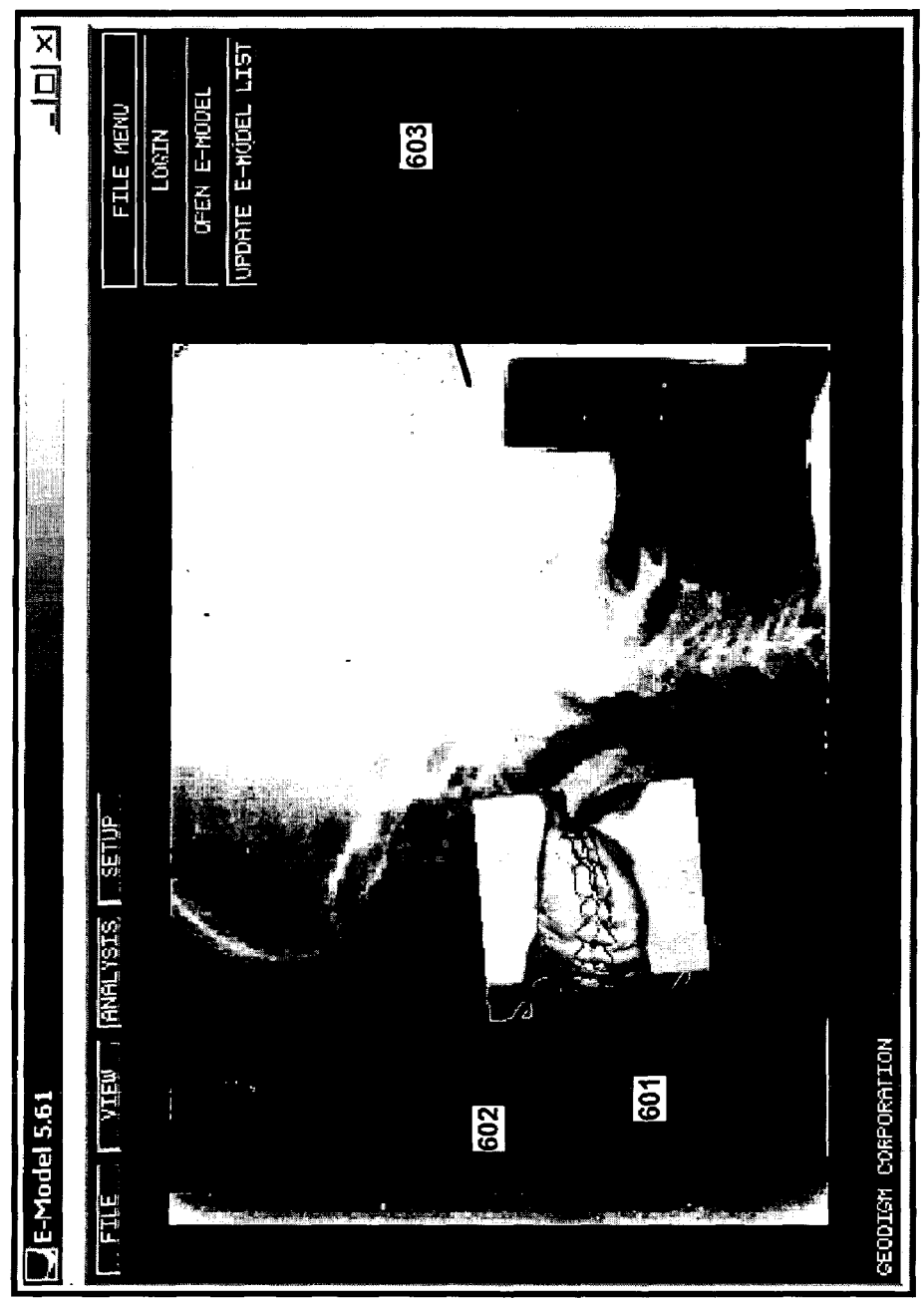
FIG. 6 illustrates an electronic image of an electronic model having an upper and low set of teeth that has been superimposed upon a other medical image of a patient according to one possible embodiment of the present invention.

FIG. 6 illustrates an electronic image of an upper and low set of teeth that has been superimposed upon another medical image of a patient according to one possible embodiment of the present invention. In order to generate an accurate color dental occlusion map, the location of the upper teeth 602 must be known relative to the location of the lower teeth 601 as the jaw opens and closes. This location data may be obtained by superimposing the electronic model for the teeth upon another image, such as an x-ray 603 shown in FIG. 6, in which common locations in both images are identified. Using these common location points, the electronic model image and the other medical image may be scaled and oriented onto a common frame of reference. While the example shown herein uses an x-ray image 603, one skilled in the art will recognize that any other medical image having sufficient resolution to permit the accurate registration of the images may be used without deviating from the spirit and scope of the present invention as recited within the attached claims.

Alternatively, the electronic model may be used to generate the color occlusion map without the use of another image if the user provides independently obtained measurements for the arc of the jaw as it opens and closes. The x-ray image 603 is useful in determining the point of rotation for the lower jaw to provide a proper definition of the motion of the upper teeth 602 relative to the lower teeth 601 as the jaw moves.

Figure 7:
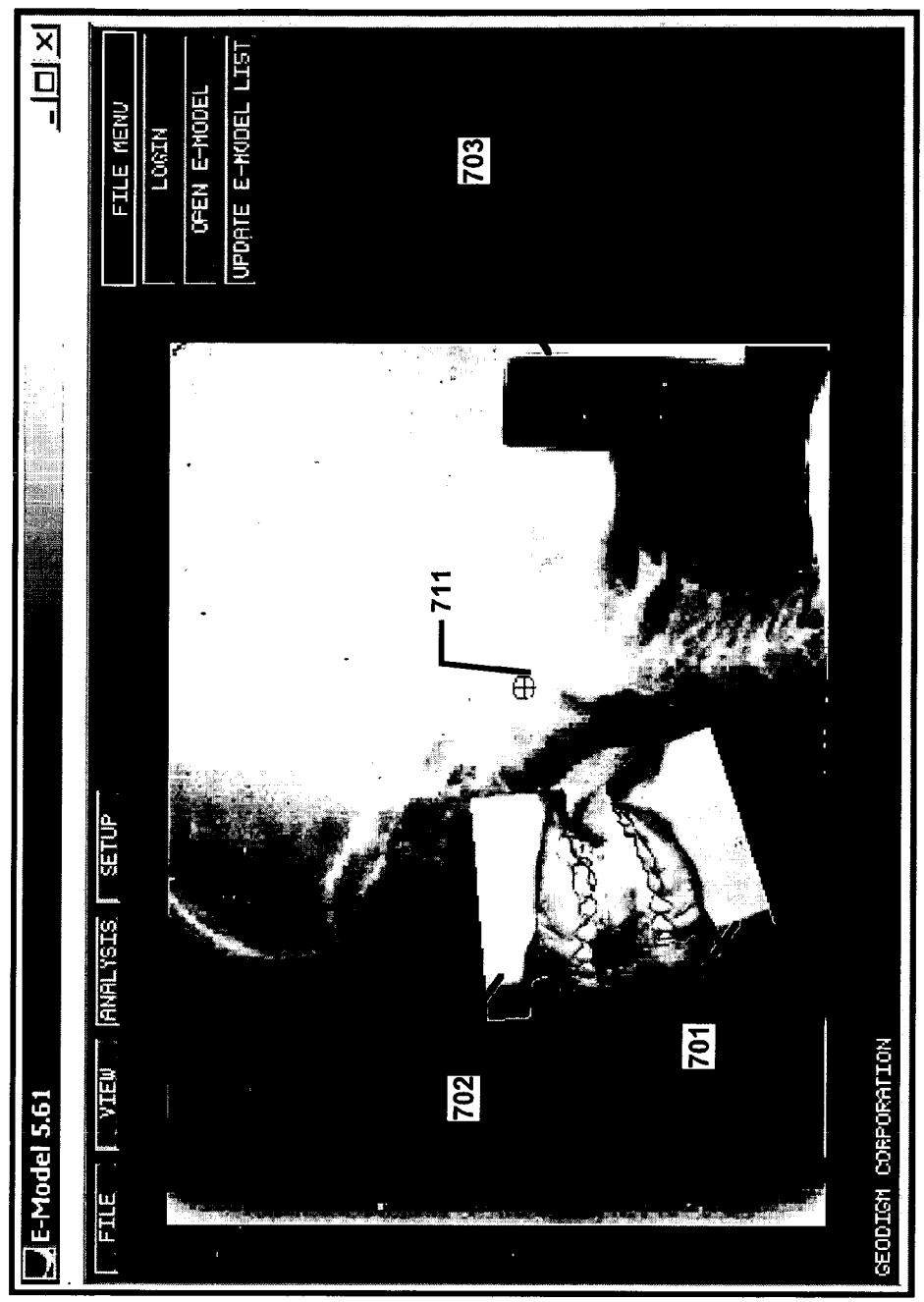
FIG. 7 illustrates an electronic image of an upper and low set of teeth that has been superimposed upon another medical image of a patient according to one possible embodiment of the present invention.

FIG. 7 illustrates an electronic image of an electronic model having an upper and low set of teeth that has been superimposed upon another medical image of a patient according to one possible embodiment of the present invention. In this image, the upper teeth 602 and the lower teeth 601 are again superimposed upon another image 603 of the patient. After the two set of images are properly scaled and registered, the point of rotation for the jaw 701 may be identified. From this point 701, and its distance from the individual teeth, the arc of motion 702 for the lower jaw 601 may be defined. Once the movement of the teeth relative to the opposing set of teeth is defined, the color dental occlusion map may be created.

Figure 8:
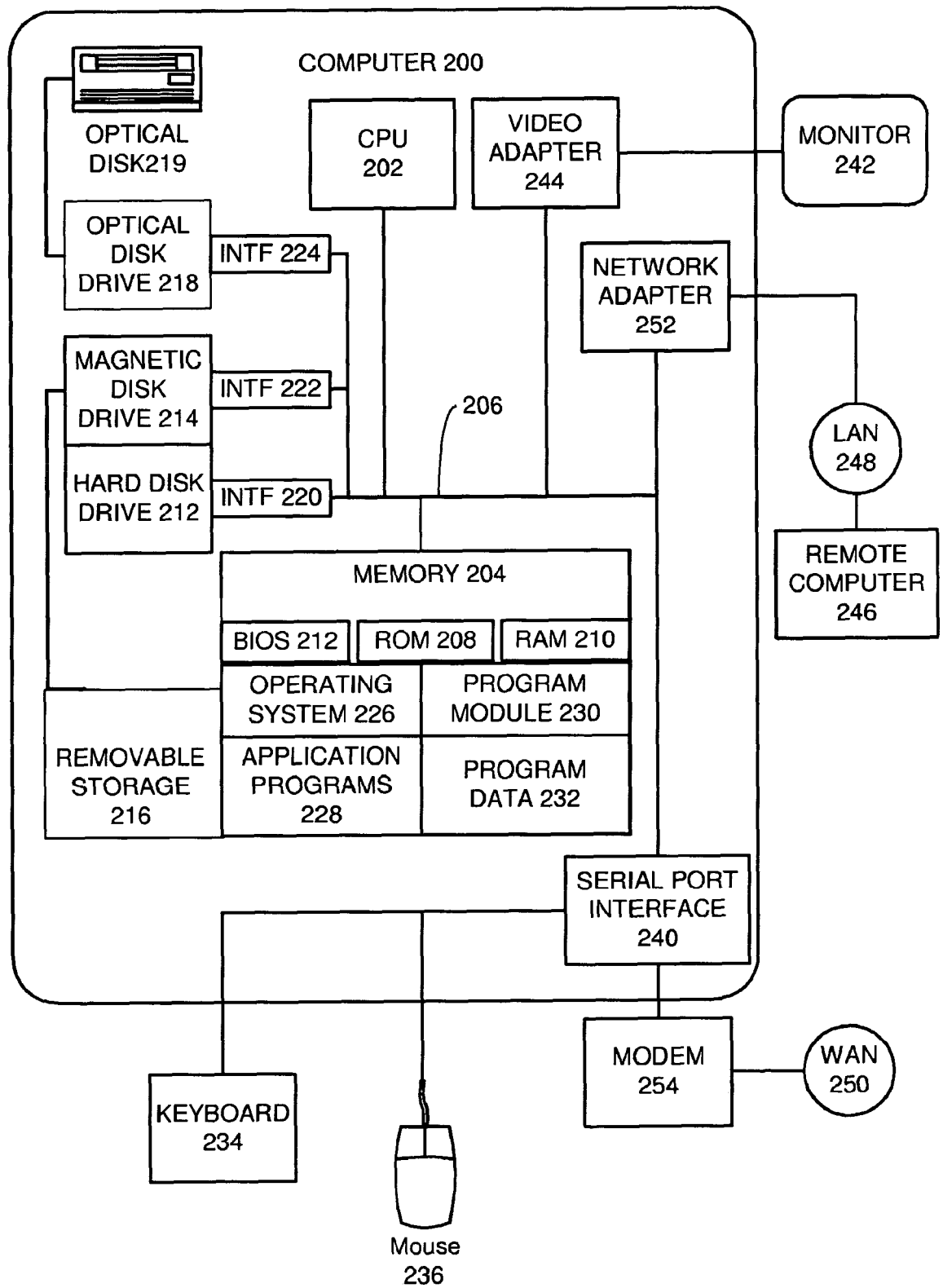
FIG. 8 illustrates an exemplary computing system useful for implementing an embodiment of the present invention.

FIG. 8 illustrates an exemplary system for implementing the invention includes a general-purpose computing device in the form of a conventional personal computer 800, including a processor unit 802, a system memory 804, and a system bus 806 that couples various system components including the system memory 804 to the processor unit 800. The system bus 806 may be any of several types of bus structures including a memory bus or memory controller, a peripheral bus and a local bus using any of a variety of bus architectures. The system memory includes read only memory (ROM) 808 and random access memory (RAM) 810. A basic input/output system 812 (BIOS), which contains basic routines that help transfer information between elements within the personal computer 800, is stored in ROM 808.

The personal computer 800 further includes a hard disk drive 812 for reading from and writing to a hard disk, a magnetic disk drive 814 for reading from or writing to a removable magnetic disk 816, and an optical disk drive 818 for reading from or writing to a removable optical disk 819 such as a CD ROM, DVD, or other optical media. The hard disk drive 812, magnetic disk drive 814, and optical disk drive 818 are connected to the system bus 806 by a hard disk drive interface 820, a magnetic disk drive interface 822, and an optical drive interface 824, respectively. The drives and their associated computer-readable media provide nonvolatile storage of computer readable instructions, data structures, programs, and other data for the personal computer 800.

Although the exemplary environment described herein employs a hard disk, a removable magnetic disk 816, and a removable optical disk 819, other types of computer-readable media capable of storing data can be used in the exemplary system. Examples of these other types of computer-readable mediums that can be used in the exemplary operating environment include magnetic cassettes, flash memory cards, digital video disks, Bernoulli cartridges, random access memories (RAMs), and read only memories (ROMs).

A number of program modules may be stored on the hard disk, magnetic disk 816, optical disk 819, ROM 808 or RAM 810, including an operating system 826, one or more application programs 828, other program modules 830, and program data 832. A user may enter commands and information into the personal computer 800 through input devices such as a keyboard 834 and mouse 836 or other pointing device. Examples of other input devices may include a microphone, joystick, game pad, satellite dish, and scanner. These and other input devices are often connected to the processing unit 802 through a serial port interface 840 that is coupled to the system bus 806. Nevertheless, these input devices also may be connected by other interfaces, such as a parallel port, game port, or a universal serial bus (USB). A monitor 842 or other type of display device is also connected to the system bus 806 via an interface, such as a video adapter 844. In addition to the monitor 842, personal computers typically include other peripheral output devices (not shown), such as speakers and printers.

The personal computer 800 may operate in a networked environment using logical connections to one or more remote computers, such as a remote computer 846. The remote computer 846 may be another personal computer, a server, a router, a network PC, a peer device or other common network node, and typically includes many or all of the elements described above relative to the personal computer 800. The network connections include a local area network (LAN) 848 and a wide area network (WAN) 850. Such networking environments are commonplace in offices, enterprise-wide computer networks, intranets, and the Internet.

When used in a LAN networking environment, the personal computer 800 is connected to the local network 848 through a network interface or adapter 852. When used in a WAN networking environment, the personal computer 800 typically includes a modem 854 or other means for establishing communications over the wide area network 850, such as the Internet. The modem 854, which may be internal or external, is connected to the system bus 806 via the serial port interface 840. In a networked environment, program modules depicted relative to the personal computer 800, or portions thereof, may be stored in the remote memory storage device. It will be appreciated that the network connections shown are exemplary, and other means of establishing a communications link between the computers may be used.

Additionally, the embodiments described herein are implemented as logical operations performed by a computer. The logical operations of these various embodiments of the present invention are implemented (1) as a sequence of computer implemented steps or program modules running on a computing system and/or (2) as interconnected machine modules or hardware logic within the computing system. The implementation is a matter of choice dependent on the performance requirements of the computing system implementing the invention. Accordingly, the logical operations making up the embodiments of the invention described herein can be variously referred to as operations, steps, or modules.

Figure 9:
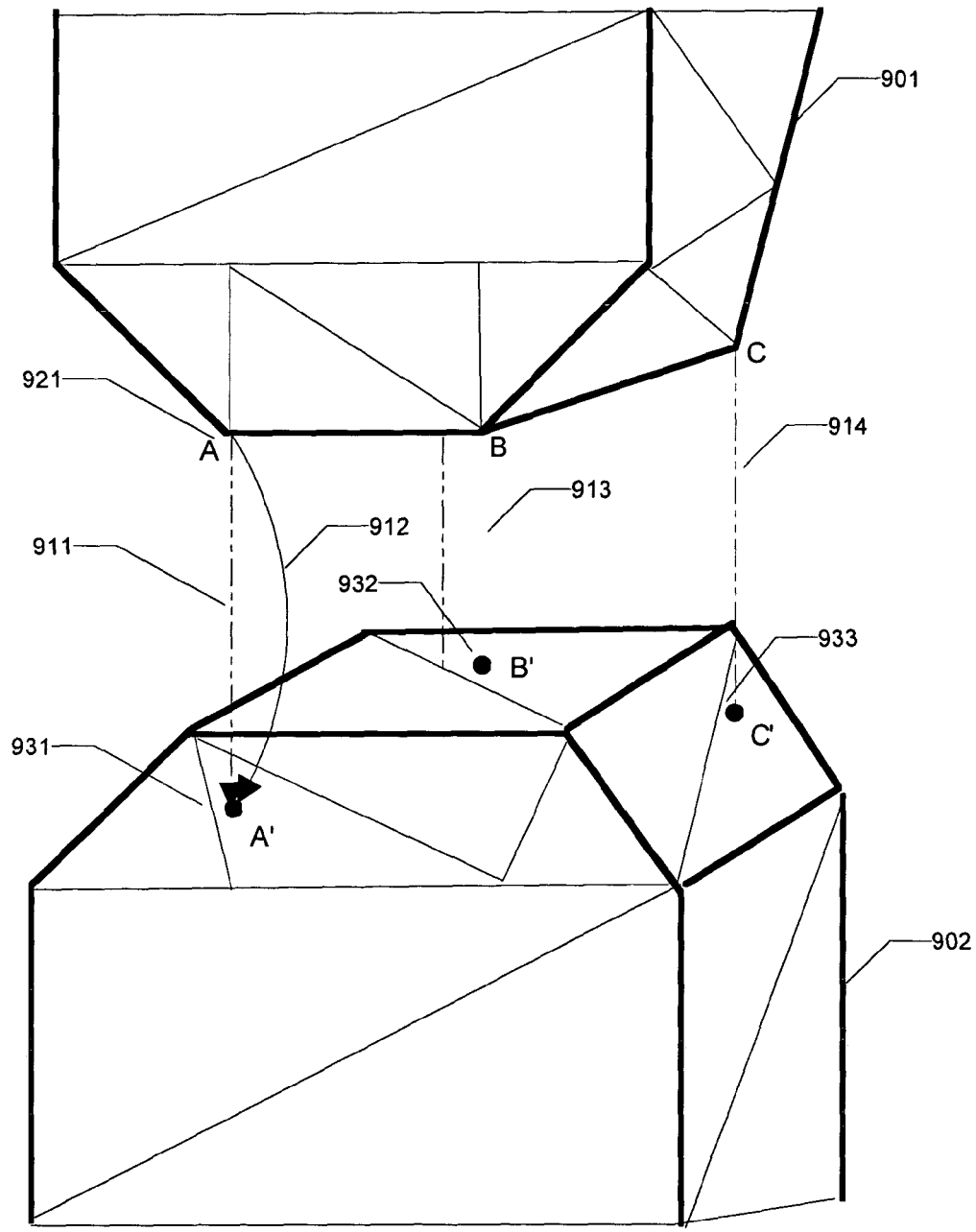
FIG. 9 illustrates two opposing teeth having multiple points of occlusion and having known separation distances according to an embodiment of the present invention.

FIG. 9 illustrates two opposing teeth having multiple points of occlusion and having known separation distances according to an embodiment of the present invention. As defined above, the electronic model represents the two opposing teeth 901, 902 as a polygonal mesh in which the mesh is constructed using a set of triangles having explicitly known locations for the respective vertices. These locations are also known relative to the point of rotation for the jaw as discussed above in FIG. 7.

Using this location data, the separation distances between the teeth may be easily determined. In calculating the separation distances, each of the vertices A 921, B 922, and C 923 are considered independently. For each of these vertices, a corresponding point A' 931, B' 932, and C' 933 are located. These corresponding points are the locations on the opposing teeth where a perpendicular distance is found between the vertices A 921, B 922, and C 923 and the surface of the opposing polygonal mesh.

Once these corresponding points, A' 931, B' 932, and C' 933, are found, a separation distance 911 may be calculated. This calculated distance may represent the perpendicular distance 911 between a vertex A 921 and its corresponding occlusion point A' 931. This calculated distance may also represent the curvilinear distance 912 between a vertex A 921 and its corresponding occlusion point A' 931 along an arc defined in reference to the point of rotation for the jaw 701. These calculated distances are determined for each vertex in both the polygonal mesh for the upper teeth 702 and the polygonal mesh for the lower teeth 701 for use in generating the color dental occlusion map.

Figure 10:
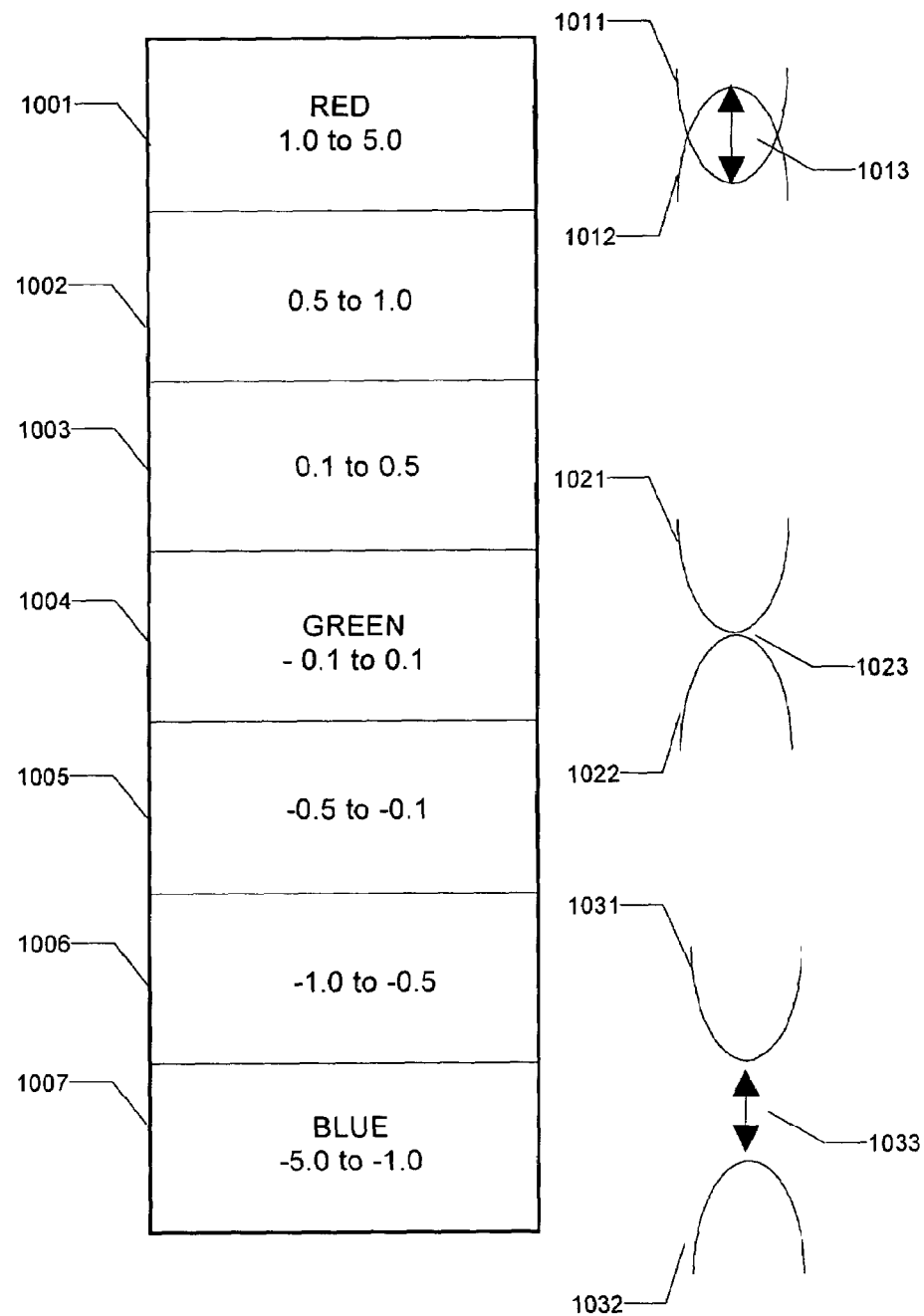
FIG. 10 illustrates a color mapping value table for use in generating color dental occlusion maps according to an example embodiment of the present invention.

FIG. 10 illustrates a color mapping value table for use in generating color dental occlusion maps according to an example embodiment of the present invention. Once the separation distances are determined, a color dental occlusion map may be generated by painting each triangle a color that corresponds to the separation distance for its vertices to the opposing teeth. In one embodiment, a color map is defined as having seven (7) different colors in which each different color represents a different range of separation distances. These separation distances may correspond to either the perpendicular distances or the curvilinear distances without deviating from the spirit and scope of the present invention.

The number of different colors, and corresponding ranges of separation distances, may be easily specified using a color mapping table shown in FIG. 10. When a triangle in a polygonal mesh is processed, its separation distance is used to index into one of the regions within the color mapping table 1001-1007 to determine the color to be used to paint the particular triangle. Thus, the electronic model will appear to be a standard electronic model with Red, Green and/or Blue locations that indicate the corresponding separation distance. Of course, one skilled in art will recognize that the number of ranges and the range values may be altered without deviating from the scope of the patent invention.

In the particular embodiment shown in FIG. 10, a Blue location corresponds to teeth 1031, 1032 having a separation 1033 between +1 and +5 mm. Similarly, a Green location corresponds to teeth 1021, 1022 having a separation 1023 between −0.1 and +0.1 mm and a Red location corresponds to teeth 1011, 1012 having a separation 1013 between 1 and 5 cm. When the triangles are painted, the surfaces may be painted in a number of ways. Typically, these surfaces are either painted using a flat (solid), single color for the triangle. The color corresponds to the color of the vertex that is closed to the opposing surface. Alternatively, a Garound or smooth surface shading may be used to provide shading between colors deferred by each of the vertices of the triangle as desired without deviating from the spirit and scope of the present invention.

Figure 11:
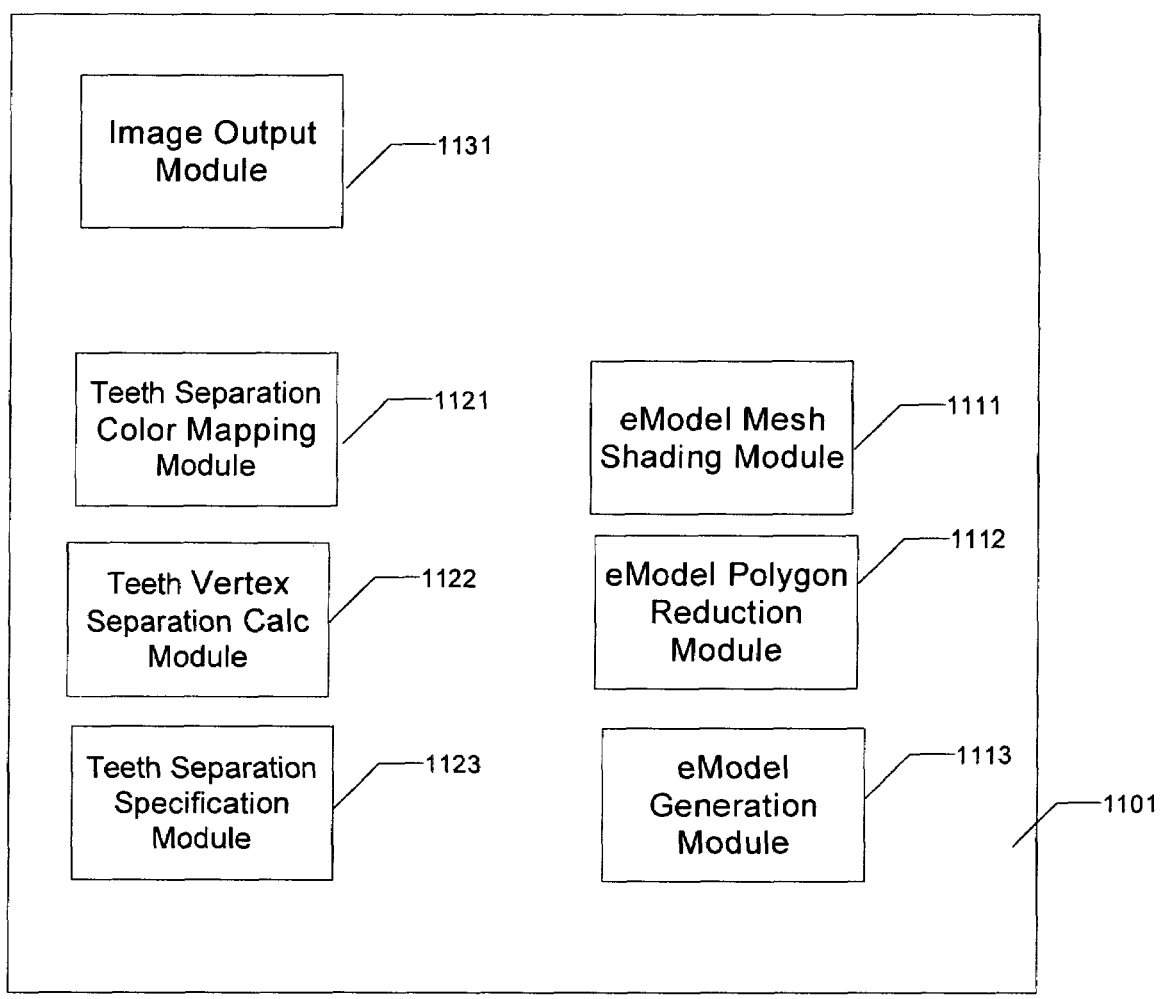
FIG. 11 illustrates a block diagram for a processing system to generate color dental occlusion maps according to another embodiment of the present invention.

FIG. 11 illustrates a block diagram for a processing system to generate color dental occlusion maps according to another embodiment of the present invention. The processing system includes a set of processing modules to perform the tasks associated with generating a color dental occlusion map. The set of processing modules includes an electronic model Mesh Shading module 1111, an electronic model polygon reduction module 1112, an electronic model generation module 1113, a teeth separation color mapping module 1121, a teeth vertex separation calculation module 1122, a teeth separation specification module 1123, and an image output module 1131.

The electronic model Mesh Shading module 1111, the electronic model polygon reduction module 1112, and the electronic model generation module 1113 perform the operations needed to generate and shade the electronic model. These modules implement the process for generating an electronic model for the teeth is described in commonly assigned U.S. patent application entitled "METHOD AND APPARATUS FOR ELECTRONIC DELIVERY OF DENTAL IMAGES", Ser. No. 09/846,037 filed Apr. 29, 2001, which is incorporated by reference.

The teeth separation color mapping module 1121 paints the triangles the color corresponding to the calculated separation distance using a color map table 1001-1007 as discussed in detail above. The s-teeth vertex separation calculation module 1122 performs the processing needed to determine the separation distance between a triangle vertex and it's corresponding mesh face along either a perpendicular or a curvilinear path as described above. The teeth separation specification module 1123 accepts input from the user to manipulate the two parts of an electronic model. This module implements the process for manipulating an electronic model for the teeth as described in concurrently filed and commonly assigned U.S. patent application entitled "METHOD AND APPARATUS FOR ELECTRONICALLY SIMULATING JAW FUNCTION", Ser. No. 60/376,111, filed Apr. 29, 2002, which is incorporated by reference. The image output module 1131 generates the image seen by a user on a display device that includes an electronic model after it has been painted using a color map.

Figure 12:
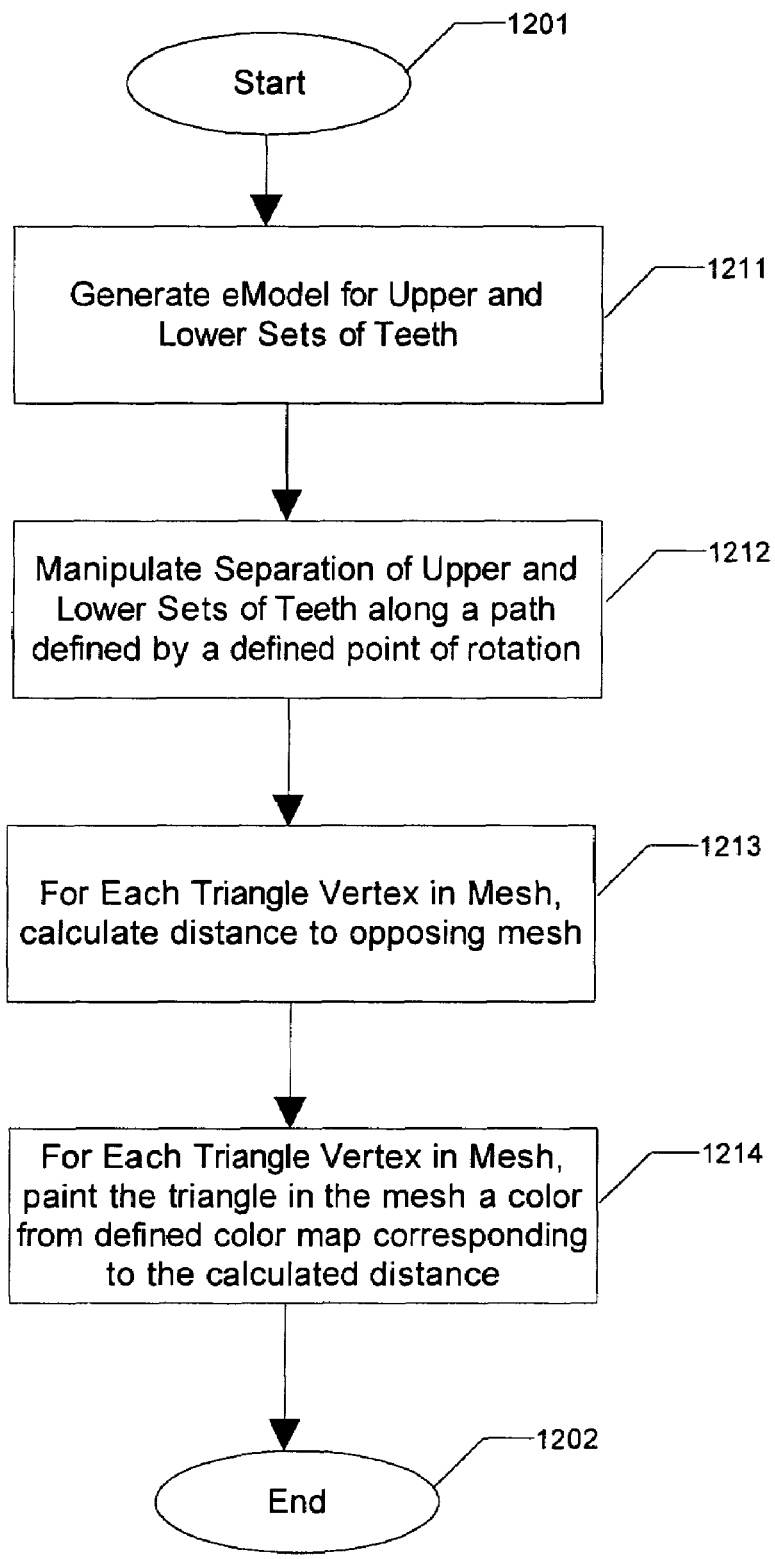
FIG. 12 illustrates a function processing flow diagram for a processing system to generate color dental occlusion maps according to yet another embodiment of the present invention.

FIG. 12 illustrates a function processing flow diagram for a processing system to generate color dental occlusion maps according to yet another embodiment of the present invention. The processing starts 1201 and an electronic model is generated for both the upper teeth and the lower teeth in module 1211. The process for generating an electronic model for the teeth is described in commonly assigned U.S. patent application entitled "METHOD AND APPARATUS FOR ELECTRONIC DELIVERY OF DENTAL IMAGES", Ser. No. 09/846,037 filed Apr. 29, 2001, which is incorporated by reference.

Once the electronic models are generated, module 1212 allows a user to move the upper and lower teeth to a desired separation distance for the upper and lower teeth in the electronic model using an input device such as a mouse. The teeth move along an arc of motion defined by a point of rotation for the jaw and the distance of the teeth from this point of rotation. The separation distance of the two parts of the electronic model then are used to calculate an individual separation distances for each vertex in the two polygonal meshes in module 1213. These individual separation distances for each vertex are then passed through a color map 1001-1007 to paint the individual triangles a color corresponding to the individual separation distance for each triangle.

The process of manipulating the separation of the two parts of the electronic model, calculating individual separation distances, and painting the triangles colors from a color map may be interactively repeated as necessary based upon input from a user. Once the electronic model has been painted a color, the electronic model may also be manipulated, rotated, zoomed, etc as the user performs analysis of the interaction of the patient's teeth.

FIG. 8 illustrates an example of a suitable operating environment in which the invention may be implemented. The operating environment is only one example of a suitable operating environment and is not intended to suggest any limitation as to the scope of use or functionality of the invention. Other well known computing systems, environments, and/or configurations that may be suitable for use with the invention include, but are not limited to, personal computers, server computers, held-held or laptop devices, multiprocessor systems, microprocessor-based systems, programmable consumer electronics, network PCs, minicomputers, mainframe computers, distributed computing environments that include any of the above systems or devices, and the like.

The invention may also be described in the general context of computer-executable instructions, such as program modules, executed by one or more computers or other devices. Generally, program modules include routines, programs, objects, components, data structures, etc. that perform particular tasks or implement particular abstract data types. Typically the functionality of the program modules may be combined or distributed in desired in various embodiments.

A computing system 1101 typically includes at least some form of computer readable media. Computer readable media can be any available media that can be accessed by the network server 110. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by the computing system 1101.

Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

The foregoing description of the exemplary embodiments of the invention has been presented for the purposes of illustration and description. They are not intended to be exhaustive or to limit the invention to the precise forms disclosed. Many modifications and variations are possible in light of the above teaching. It is intended that the scope of the invention be limited not with this detailed description, but rather by the claims appended hereto. Thus the present invention is presently embodied as a method, apparatus, computer storage medium or propagated signal containing a computer program for electronically generating a color dental occlusion map within electronic model images.

What is claimed is:

1. A method for electronically generating a color dental occlusion map within electronic model images on a computing device including a processor and memory, the method comprising:
    obtaining an electronic model of an upper set of teeth and a lower set of teeth from the memory of the computing device, the upper and lower sets of teeth being represented by opposing polygonal meshes, each polygonal mesh including a plurality of triangles, a first one of the polygonal meshes is configured to pivot at a point of rotation relative to a second one of the polygonal meshes, wherein at least one point on each triangle of the first polygonal mesh travels through a respective series of points that defines an arc of motion when the first polygonal mesh pivots relative to the second polygonal mesh;
    manipulating a spatial separation between the first polygonal mesh and the second polygonal mesh by instructing the processor of the computing device to pivot the first polygonal mesh at the point of rotation;
    for at least one point on each triangle of the first polygonal mesh, instructing the processor to calculate a separation distance to an opposing point on one of the triangles of the second polygonal mesh, the distance being determined by the processor at least partially based on the arc of motion along which the respective point of the first polygonal mesh travels;
    for each triangle in the first polygonal mesh, instructing the processor to paint the triangle of the first polygonal mesh a color corresponding to the respective separation distance between the point on the triangle and the corresponding opposing point on the second polygonal mesh; and
    wherein manipulating the spatial separation changes the separation distances between the points of the first polygonal mesh and the corresponding opposing points of the second polygonal mesh.

2. The method according to claim 1, further comprising: —generating the electronic model including:
    scanning a surface of a physical model of teeth; and
    generating at least the first polygonal mesh to correspond to the scanned surface; and
    storing the electronic model in the memory of the computing device.

3. The method according to claim 1, wherein the manipulating the spatial separation comprises accepting input from a user with an input device, the input indicating how the first and second polygonal meshes are to be manipulated.

4. The method according to claim 1, further comprising defining the point of rotation including:
    displaying an electronic image of a skull of the patient to the user on a display device;
    displaying the electronic model over the electronic image of the skull; and
    accepting input from a user indicating the point of rotation.

5. The method according to claim 4, wherein the electronic image corresponds to a digital representation of an x-ray.

6. The method according to claim 1, wherein the painting the triangles of at least the first polygonal mesh paints each triangle a flat single color chosen from a color value table.

7. The method according to claim 1, wherein the painting the triangles of at least the first polygonal mesh uses a smooth surface shading applied to a color chosen from a color value table.

8. The method according to claim 1, wherein the painting the triangles of at least the first polygonal mesh uses a Gouraud shading applied to a color chosen from a color value table.

9. A computer program product embodied on a computer-readable medium and comprising code that, when executed, causes a computer to implement a method to generate a color dental occlusion map, the method comprising:

providing a computing system, wherein the computing system includes distinct software modules, and wherein the distinct software modules include a generation module, a separation specification module, a separation calculation module, and separation mapping module;

generating an electronic model of an upper set of teeth and a lower set of teeth, the electronic model including a first triangular mesh representing the upper set of teeth and a second triangular mesh representing the lower set of teeth, the triangular meshes including a plurality of triangles, each triangle having a respective vertex, wherein each triangular mesh is configured to pivot at a point of rotation relative to the other triangular mesh, wherein each vertex of each triangle of one of the triangular meshes travels along a corresponding arc of motion when the triangular mesh pivots relative to the other triangular mesh, wherein the generating of the electronic model is performed by the generation module;

manipulating a spatial separation of the first triangular mesh representing the upper set of teeth relative to the second triangular mesh representing the lower set of teeth by pivoting at least one of the triangular meshes about the point of rotation, wherein the manipulating is performed by the separation specification module;

calculating a curvilinear distance from at least one of the triangle vertices of each triangle in at least a portion of the first triangular mesh to a corresponding triangle vertex of the second triangular mesh, the curvilinear distance being determined at least partially based on the arc of motion corresponding to the vertex, wherein the calculating is performed by the separation calculation module; and painting each of the triangles in the portion a color corresponding to the distance calculated for the respective triangle vertices, the painting being performed by the separation mapping module.

10. The computer program product according to claim 9, wherein manipulating the spatial separation of the triangular meshes comprises:

superimposing the electronic model over an electronic medical image showing a dentition of a patient;

determining the point of rotation based on the electronic medical image.

11. The computer program product according to claim 9, wherein the point of rotation is defined using an electronic image of an x-ray of a skull.

12. The computer program product according to claim 9, wherein painting each of the triangles comprises painting each triangle a flat single color chosen from a color value table.

13. The computer program product according to claim 9, wherein painting each of the triangles uses a smooth surface shading applied to a color chosen from a color value table.

14. A method for electronically generating a color dental occlusion map on an electronic display device for a patient, the method being implemented using an electronic computing system including a computer processor, the method comprising:

generating on the computer processor a first electronic model representing a first set of teeth of the patient and a second electronic model representing a second set of teeth of the patient, a surface of each electronic model being formed from a polygonal mesh, each polygonal mesh including a plurality of polygons, each of the electronic models being configured to rotate relative to each other at a rotation point;

graphically displaying the polygonal mesh of each electronic model on the electronic display device;

positioning the second electronic model relative to the first electronic model on the electronic display device;

calculating on the computer processor a distance from at least one point on at least one polygon in the polygonal mesh of the first electronic model to a corresponding point on at least one polygon in the polygonal mesh of the second electronic model, the distance being determined at least partially based on the point of rotation and a distance extending between the point of rotation and the point on the polygonal mesh of the first electronic model;

painting on the electronic display device the polygon associated with the point a color to indicate the distance calculated;

moving at least one of the electronic models such that the first set of teeth and the second set of teeth are shown on the displayed device as arranged in an occluded position;

recalculating on the computer processor the distance from the point on the polygon in the polygonal mesh of the first electronic model to the corresponding point in the polygonal mesh of the second electronic model; and painting on the electronic display device the polygon associated with the point on the first polygonal mesh a different color to indicate the recalculated distance.

15. The method according to claim 14, wherein calculating a distance includes calculating a distance from a plurality of polygon vertices in the polygonal mesh of the first electronic model to corresponding polygon vertices in the polygonal mesh of the second electronic model.

16. The method according to claim 15, wherein painting a polygon includes painting a plurality of polygons, each polygon corresponding to one of the plurality of polygon vertices.

17. The method according to claim 14, wherein painting a polygon includes painting the polygon a flat, single color.

18. The method according to claim 14, wherein painting a polygon includes painting the polygon multiple colors using smooth surface shading.

19. The method according to claim 18, wherein painting the polygon multiple colors includes painting the polygon using Gouraud shading.

20. The method according to claim 14, wherein calculating a distance includes calculating a curvilinear distance.

21. The method according to claim 14, wherein the first electronic model corresponds with an upper set of teeth and the second electronic model corresponds with a lower set of teeth.

22. The method according to claim 14, further including determining the point of rotation based on an electronic medical image.

23. The method of claim 1, wherein the at least one point on each triangle of the first polygonal mesh comprises three vertices of the triangle.

24. The method of claim 14, wherein calculating on the computer processor the distance comprises calculating on the computer processor the distance between a vertex of the polygon on the polygonal mesh of the first electronic model to a corresponding polygonal vertex on the polygonal mesh of the second electronic model.

* * * * *